United States Patent [19]
Ferrari et al.

[11] Patent Number: 5,875,782
[45] Date of Patent: *Mar. 2, 1999

[54] METHODS AND DEVICES FOR MINIMALLY INVASIVE CORONARY ARTERY REVASCULARIZATION ON A BEATING HEART WITHOUT CARDIOPULMONARY BYPASS

[75] Inventors: Richard M. Ferrari, Saratoga; Charles S. Taylor, San Francisco, both of Calif.; Jack W. Lasersohn, East Hampton, N.Y.; Federico J. Benetti, Rosario, Argentina; Jodi J. Akin, Concord, Calif.; Richard Ginn, San Jose, Calif.; Amr Salahieh, Campbell, Calif.

[73] Assignee: Cardiothoracic Systems, Inc., Cupertino, Calif.

[*] Notice: This patent issued on a continued prosecution application filed under 37 CFR 1.53(d), and is subject to the twenty year patent term provisions of 35 U.S.C. 154(a)(2).

[21] Appl. No.: 752,741

[22] Filed: Nov. 14, 1996

[51] Int. Cl.$^6$ .................................................. A61B 19/00
[52] U.S. Cl. ............................. 128/898; 604/49; 600/235
[58] Field of Search ................................ 128/898; 623/1; 604/49, 264, 280; 606/170; 600/235

[56] References Cited

U.S. PATENT DOCUMENTS 5,634,937  6/1997  Mollenauer et al. .

FOREIGN PATENT DOCUMENTS

WO 96/32882  10/1996  WIPO .

OTHER PUBLICATIONS

Benetti et al. "Direct myocardial revascularization without extracorporeal circulation." Chest 100:312–316, Aug. 1991.

*Primary Examiner*—Mickey Yu
*Assistant Examiner*—Kelly O'Hara
*Attorney, Agent, or Firm*—Carol LaSalle

[57] ABSTRACT

Methods and devices for revascularization of a patient's coronary artery system which obviate the need to place the patient on cardiopulmonary bypass. A method is provided for revascularizing a patient while the-heart is beating, and includes performing at least one minimally invasive coronary artery bypass graft procedure, or other cardiac surgical procedure, and contemporaneously performing at least one catheter-based procedure in at least one coronary artery. The catheter-based procedure(s) may be either therapeutic or diagnostic or both, and may involve delivering at least one catheter to a coronary artery via a surgical or percutaneous opening in the thoracic cavity or via a percutaneous opening at a location peripheral to the thoracic cavity. The catheter-based procedure or procedures is performed contemporaneously with the bypass graft procedure, and specifically prior to, during, or after anesthetizing the patient for purposes of the bypass graft procedure. An arterial access device is also provided for central cannulation and direct intraoperative catheterization of a patient's coronary artery system on a beating heart. The device includes a tubular member, such as a cannula, having a proximal end and a distal end, and an elongated puncturing member, such as a trocar, which is slideably disposed within the tubular member. The puncturing member has a sharp distal end for puncturing through the wall of a coronary lumen. The arterial access device further includes a sealing member for engaging the coronary lumen wall at the puncture site in order to minimize the leakage of blood from the puncture site.

17 Claims, 7 Drawing Sheets

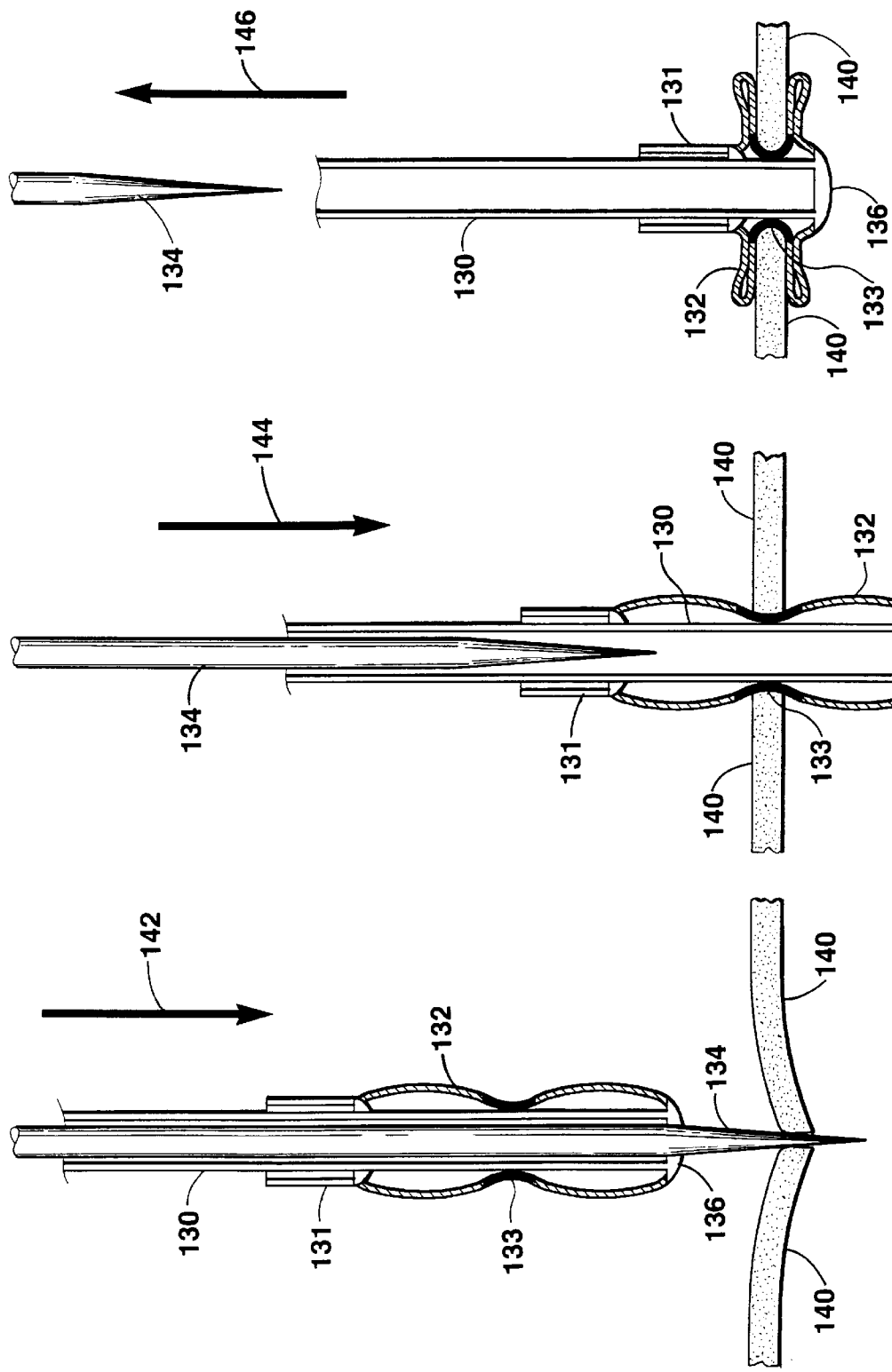

METHODS AND DEVICES FOR MINIMALLY INVASIVE CORONARY ARTERY REVASCULARIZATION ON A BEATING HEART WITHOUT CARDIOPULMONARY BYPASS

FIELD OF THE INVENTION

The present invention relates generally to methods and devices for performing cardiac procedures. More particularly, the present invention relates to methods and devices of coronary revascularization without placing the patient on cardiopulmonary bypass support.

BACKGROUND OF THE INVENTION

It is known that long-term relief from coronary artery disease and improved longevity may be achieved through complete revascularization of a patient who suffers from coronary artery stenosis or infarction of the myocardium. Revascularization by coronary artery bypass grafting (CABG) has long been the gold standard of total revascularization. In particular, a CABG procedure in which the left internal mammary artery (LIMA) is anastomosed to the left anterior descending (LAD) artery is well accepted as providing a superior survival rate. However, conventional CABG procedures have many drawbacks. Conventional CABG procedures require the patient to be placed on cardiopulmonary bypass (CPB) support, and typically require either a sternotomy or major thoracotomy to be employed. It is well known in the medical community that CPB produces many deleterious effects to the patient. A sternotomy is highly traumatic to the patient, requiring a lengthy recovery period and having some risk of life-threatening infection. As for a major thoracotomy, a patient typically endures much postoperative pain from such a procedure. Additionally, the use of Heparin, which is commonly prescribed for anticoagulation during a CABG procedure, carries its own potential risks and complications which are commonly known to surgeons. Furthermore, a CABG approach is often limited where the subject artery or arteries have multiple segmental or diffuse stenoses (e.g., the apex of the LAD), or where the arterial size is unacceptable for grafting.

Consequentially, advanced catheter-based therapies, and percutaneous transluminal coronary angioplasty (PTCA) in particular, have risen in popularity in order to provide less invasive means for treating coronary artery stenosis. These methods have the advantage of being less traumatic and require a shorter recovery time. However, they are not without their own limitations. It is known that PTCA carries a significantly higher restenosis and reintervention rates than a CABG procedure for the left anterior diagonal (LAD) artery, which provides the majority of blood flow to the left ventricle which is responsible for cardiac output to the vital organs. About 80–90% of patients suffering from symptomatic atherosclerosis require revascularization of the LAD. Accordingly, the use of catheter-based therapies alone to provide complete revascularization is limited in many cases.

Under certain conditions, operative transluminal coronary angioplasty (OTCA) has been used as an adjunct to CABG in the course of one operation. Most commonly, OTCA has been performed through the arteriotomy used for the grafting site, and then only in the context of standard CPB. Unfortunately, OTCA has not shown a proven record of long-term patency rates.

Considering all of the above, there is a need to for an improved method of revascularization which optimizes the individual advantages of CABG procedures and catheter-based interventions while eliminating some of the drawbacks of these procedures when performed independently of the other. Such a method would preferably involve a "hybrid" approach comprising a CABG procedure performed in conjunction with catheter-based interventions and/or diagnosis. The method would preferably eliminate some of the drawbacks of conventional CABG procedures and, in particular, would eliminate the need for CPB for the reasons discussed above. Applicant's copending U.S. patent application, entitled "Method for Coronary Artery Bypass" and having Ser. No. 08/419,991, discloses a method for performing "Minimally Invasive Direct Coronary Artery Bypass Grafting" (MIDCAB™) on a beating heart, and is hereby incorporated by reference in its entirety.

The MIDCAB method involves a direct access or "direct vision" approach in which bypass grafting is accomplished through a small surgical "window" in the patient's chest. This window is preferably a minimal thoracotomy formed by an intercostal incision generally less than 12 cm. Access to the heart is provided by a retractor which spreads the ribs both horizontally and vertically. Other access ports through the thoracic cavity may be employed if necessary but are not required. The MIDCAB method includes techniques which eliminate the need for CPB while still providing a substantially bloodless and stable operating field for ensuring a successful anastomosis. Most advantageously, the portion of the heart proximate to the vessel to be bypassed is stabilized, and a segment of the vessel is occluded, preferably both proximally and distally to the arteriotomy site. This is accomplished by providing ligating stay sutures at the appropriate locations of the vessel or by other more sophisticated stabilization means which are discussed in more detail below. The method is primarily directed to grafting the LIMA to either the LAD, the diagonal (Dx) and circumflex (Cx) arteries; the latter grafts being typically accomplished by means of a "T-graft" with the radial artery from the LIMA sequentially to the Dx and Cx arteries.

Furthermore, the MIDCAB approach is far less traumatic and less painful than conventional approaches which require CPB and employ a sternotomy or a major thoracotomy. Additionally, the MIDCAB method has been shown to obviate the need for Heparin or require only minor doses.

SUMMARY OF THE INVENTION

The present invention generally involves methods for complete or partial revascularization of a patient's coronary artery system which do not require placing the patient on CPB. One aspect of the present invention involves a hybrid approach to revascularization which employs a MIDCAB procedure or other cardiac surgical procedure in combination with catheter-based revascularization interventions. A MIDCAB procedure, for example, may be employed when the LAD needs revascularization, and one or more catheter-based procedures, such as PTCA for example, may be used to revascularize other arteries which are not amenable to bypass grafting or are otherwise unreachable by a MIDCAB procedure.

This hybrid approach is flexible, providing for either intraoperative catheter procedures (i.e., where catheters are introduced "directly" through a surgical opening in the patient's thoracic cavity) or percutaneous catheter procedures (i.e., where catheters are introduced through small incisions peripherally via, for example, a femoral artery). For "direct" intraoperative catheterization, the present invention provides improved methods and surgical instruments that allow intraoperative catheter access to coronary arteries directly by means of "central cannulation" of a coronary lumen such as the aorta or an artery proximate to the aorta, such as the left subclavian artery, the left common carotid artery, and the brachiocephalic trunk, commonly referred to as the innominate artery.

The methods and devices of the present invention also enhance a physician's ability to achieve complete coronary revascularization in the course of one operation wherein the MIDCAB procedure is performed "contemporaneously" with one or more catheter-based procedures, preferably in one operating room and during a single application of anesthesia in order to reduce the costs and to maximize the efficiency of the revascularization process.

More specifically, in one embodiment of the present invention, a method of revascularization is provided which includes performing at least one minimally invasive coronary artery bypass graft procedure and contemporaneously performing at least one catheter-based procedure in at least one coronary artery while the heart is beating. The minimally invasive coronary artery bypass graft procedure comprises stabilizing the beating heart proximate to the coronary artery to be bypassed, with access preferably provided via a minimal thoracotomy in the thoracic cavity. The catheter-based procedure(s) may be either therapeutic or diagnostic or both, and may involve delivering at least one catheter to a coronary artery via a surgical or percutaneous opening in the thoracic cavity or via a percutaneous opening at a location peripheral to the thoracic cavity. The catheter-based procedure is performed contemporaneously with the bypass graft procedure, and specifically prior to, during, or after anesthetizing the patient for purposes of the bypass graft procedure.

Another embodiment of the invention involves a method of revascularization performed on a patient without placing the patient on cardiopulmonary bypass. The method includes forming at least one surgical opening in the patient's thoracic cavity, and through a surgical opening, forming at least one entry site in the wall of a coronary lumen. Preferably, the coronary lumen is selected from the group consisting of the aorta, the left subclavian artery, the left common carotid artery, and the innominate artery. At least one elongated surgical instrument, such as a catheter, is then introduced in the patient's coronary arterial system through the entry site for treatment of the patient's coronary arterial system. The entry site is formed by cannulating the coronary lumen. A particular example of the procedure just described includes forming at least two surgical openings in the patient's thoracic cavity wherein the subclavian artery is cannulated through one of the two surgical openings.

Yet another aspect of the present invention involves accessing a patient's coronary arterial system for the purpose of coronary revascularization, in which heart contractions are not artificially halted, by first forming at least one surgical opening in the patient's thoracic cavity, introducing an arterial access device into the thoracic cavity via a surgical opening, and then puncturing the wall of a coronary lumen with the arterial access device. The arterial access device includes a cannula which is designed to remain in the lumen wall upon puncturing. At least one elongated surgical instrument can then be introduced into the patient's coronary arterial system through the cannula to perform some interventional or diagnostic function. This procedure further includes the step of sealing the lumen wall at the puncture site around the cannula wherein the leakage of blood at the puncture site is minimized.

The present invention also provides for a method of intraoperative catheterization performed in conjunction with at least one minimally invasive cardiac surgical procedure. This method involves creating at least one minimally invasive opening in the patient's thoracic cavity through which the cardiac surgical procedure is performed, forming an entry site in the wall of a coronary lumen, introducing one or more catheters through the one entry site, and advancing the distal end of a catheters through the coronary lumen to a target site within a coronary artery. Each of these steps is performed while the patient's heart is beating. The coronary lumen through which the entry site is made depends on the particular clinical diagnosis. The cardiac surgical procedure performed may be, but is not limited to, a coronary artery bypass graft.

The present invention further provides for devices and a system of devices for performing the methods described above. In particular, an arterial access device is provided which includes a tubular member, such as a cannula, having a proximal end and a distal end, and an elongated puncturing member, such as a trocar, which is slideably disposed within the tubular member. The puncturing member has a sharp distal end for puncturing through the wall of a coronary lumen. The arterial access device further includes a sealing member for engaging the coronary lumen wall at the puncture site in order to minimize the leakage of blood from the puncture site. The sealing member may be, for example, a tubular braid or an expandable mechanism.

The present invention also provides for an intraoperative catheterization system which includes an arterial access device for forming an entry site in the wall of a coronary lumen via an opening in the patient's thoracic cavity. The arterial access device comprises a cannula and at least one flexible catheter which is adapted for direct insertion into the coronary lumen via the cannula and which is positionable at the ostium of a selected coronary artery to be revascularized. The cannula has a length not substantially more than 30 cm. The catheter includes a tip portion having a length not substantially more than 10 cm, a shaft portion having a length not substantially more than 50 cm, and a profiled portion between the tip and shaft portions. The profiled portion of the catheter is a bend having an angle between about 20° and 90°.

Preferably, at least one of the catheters of the intraoperative catheter system is a guide catheter which has a tip design and a length adapted for direct entry via central cannulation through the aorta, subclavian, or other artery, and for facilitating the proper delivery of therapeutic and diagnostic catheters or other surgical instruments to the ostia of the coronary arteries selected for revascularization.

BRIEF DESCRIPTION OF THE DRAWINGS

FIGS. 3A–C are schematic representations depicting the operation of the device of FIG. 2 upon insertion into a coronary lumen of a patient.

DETAILED DESCRIPTION OF THE INVENTION

Figure 1A:
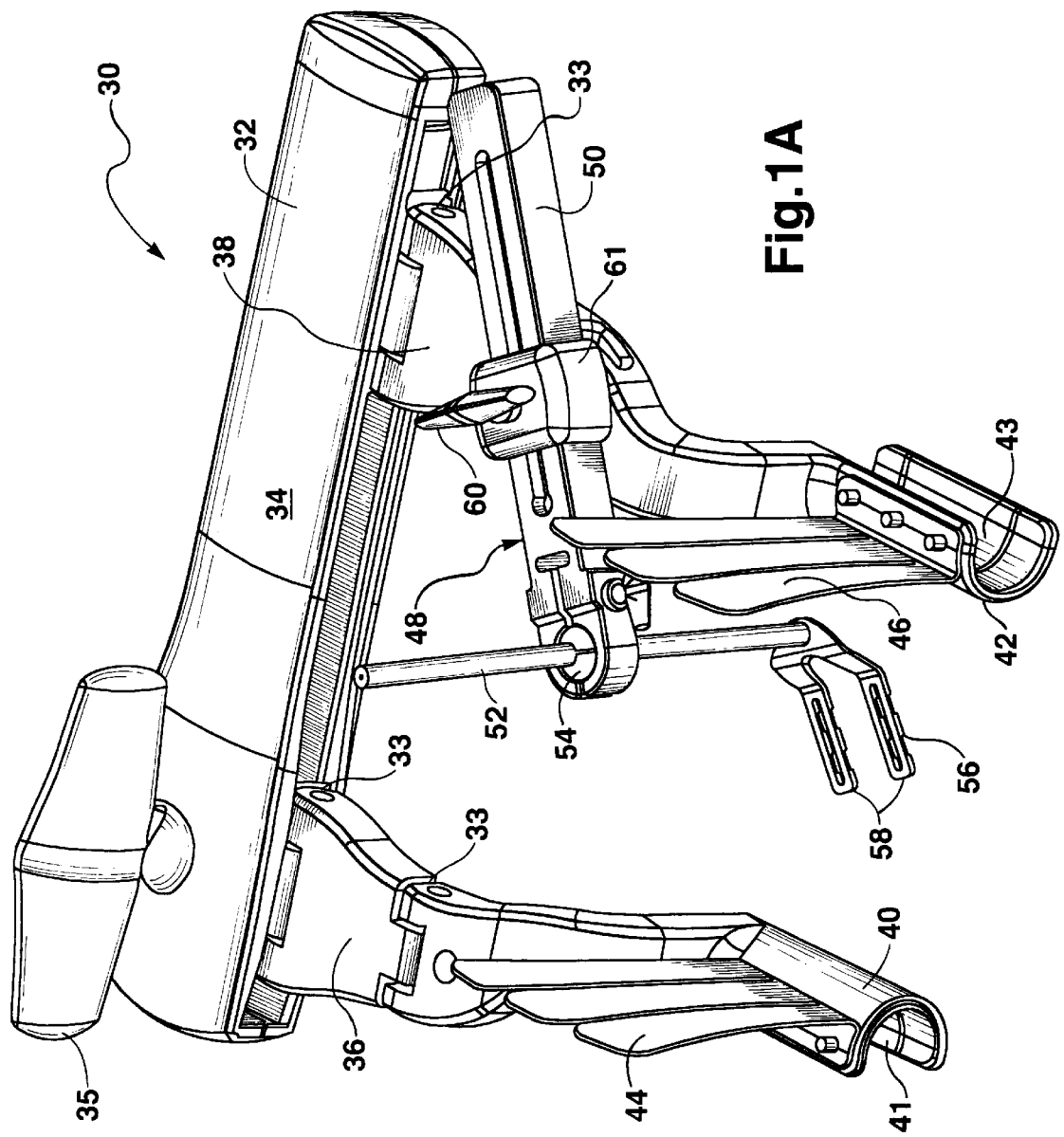
FIG. 1A is an isometric view of a device used to facilitate minimally invasive access to the patient's cardiac area.

The methods of the present invention are suitable for performing complete or partial revascularization of a patient's coronary artery system where the patient is not placed on CPB; hence, the revascularization procedure(s) are intended to be performed while the patient's heart is beating. The revascularization method(s) involves, at least in part, one or more catheter-based treatments performed contemporaneously with one or more cardiac surgical procedures. Such catheter-based therapies include but are not limited to angioplasty, perfusion, stent placement, extraction, ablation, and drug delivery. Several cardiac surgical procedures are suitable in the context of the present invention including, but not limited to, CABG, electrophysiology procedures, myocardial ablation therapy, congenital heart repairs, and valvuloplasty. Preferably, such contemporaneously performed cardiac surgical procedure is a MID-CAB procedure.

By "contemporaneously," it is contemplated that all revascularization procedures be performed in spacial and/or temporal proximity to each other, and preferably in one room (i.e., the operating room) during the course of a single anesthetization of the patient. Also, the procedures may be performed sequentially or simultaneously.

All catheter and surgical procedures are performed through one or more minimally invasive surgical openings. Preferably, only one minimally invasive surgical opening is made if the procedure(s) are done under direct vision through the patient's thoracic cavity; however, more openings may be necessary if catheters are peripherally introduced via the femoral arteries and/or a thoracoscope is used. With respect to the catheter-based procedures, the present invention provides for the introduction of catheters either directly through the thoracic cavity or peripherally through other percutaneous openings.

Procedures involving peripherally (often referred to as "percutaneously") inserted catheters, such as with PTCA, provide for the insertion of one or more catheters via a percutaneous penetration at a location peripheral to the diseased coronary artery. Most commonly, a catheter is introduced into one of the patient's femoral arteries at the patient's groin, and then directed to the target site in a selected coronary artery. The arterial length to be traversed in such a procedure involves a risk of dissection of the arterial lining, (e.g., either in the stenotic plaque or the arterial intima). This dissection allows blood flow between the arterial wall and the dissected lining which may constrict the flow passage or cause a section of the dissected lining, commonly called a "flap," to be forced into the flow passageway thereby partially or completely blocking the blood flow through the artery. This risk may be minimized if the coronary artery to be treated is accessed directly through the thoracic cavity, rather than accessed peripherally.

On the other hand, intraoperative catheterization by means of cannulation of a coronary lumen under direct vision, or central cannulation as it is commonly referred, has its own risks. Of particular concern is the risk of stroke to the patient caused by plaque which may be broken loose from the endothelial lining of the coronary lumen upon cannulation of the coronary lumen.

Thus, while both percutaneous and intraoperative catheter techniques have their respective advantages and associated risks, the flexibility of the present invention allows a physician to employ the technique which is most advantageous for the patient based on the particular clinical diagnosis.

The various methods of the present invention for performing revascularization of a patient's coronary artery system will now be described in more detail. A MIDCAB procedure is used herein as an example of a contemporaneous cardiac surgical procedure which is performable in the context of the methods of the present invention, however, it is readily appreciated that the techniques and instruments discussed herein may be applied to other procedures (examples mentioned above) depending on the clinical diagnosis. In addition, the MIDCAB procedure is described herein as being performed through a minimal left thoracotomy, however, it is also readily appreciated that the procedure may be accomplished by means of a minimal right throracotomy, a minimal sternotomy, or smaller percutaneous openings in the thoracic cavity and by use of a thoracoscope. For purposes of describing intraoperative catheterization methods of the present invention, exemplary treatments and particular types of catheters are discussed. The description following is not intended to limit the present invention to these specific procedures, treatments, and instruments, but is intended to be only exemplary of the present invention.

In addition, a particular order of revascularization procedures has been chosen for purposes of discussion, however, this order is not intended to be limiting to the present invention. In fact, the order in which the revascularization procedures are performed is patient-specific and depends on the clinical diagnosis in each case. For example, a particular diagnosis might require that a MIDCAB or other cardiac surgical procedure be performed first followed by one or more catheter-based therapies. Starting with a MIDCAB procedure which successfully establishes critical blood flow through the LAD, for example, is advantageous where it is then determined that the need for interventional catheter methods is obviate.

On the other hand, the diagnosis might require the physician to first perform a PTCA procedure, for example, on a selected coronary artery, either before or after the patient is anesthetized. The success of the PTCA procedure may then be assessed by use of one or more diagnostic catheter methods. Upon completion of catheterization procedures, one or more bypass grafts may then be employed on the same or other coronary arteries.

In another case, a MIDCAB procedure may be performed simultaneously with a catheter-based procedure, wherein the catheters are inserted intraoperatively, percutaneously, or both intraoperatively and percutaneously. Notwithstanding a particular clinical diagnosis and a particular order of procedures, under the method of the present invention, all revascularization procedures are performed contemporaneously within a single period of time for which the patient may be completely anesthetized, and preferably in one operating room, on one operating table, and by one physician.

Turning now to a detailed description of the surgical process, the patient undergoing the procedure is prepared for cardiac surgery, and is placed under general anesthesia. Once anesthetized, the patient may be intubated with a double-lumen endobronchial tube, for example, which allows for the selective ventilation or deflation of the right and left lungs. As all procedures of the present invention are performed on a beating heart, no steps are taken to place the patient on CPB and administer cardioplegia solution as would otherwise be done at this point in a conventional operation.

After the patient has been prepared as described above, the physician commences the revascularization surgery by making one or more percutaneous surgical openings. The number of percutaneous openings and the optimal location of each opening will depend on several factors: (1) the location of the arteries to be revascularized by means of a MIDCAB procedure, if any; (2) the location of the arteries to be revascularized by means of catheter-based procedures; and (3) the anatomy and physiology of the particular patient.

At least one surgical opening will be formed in the thoracic cavity to allow for the introduction of surgical instruments for the designated surgical procedure for revascularizing at least one coronary artery or repairing or reconstructing a valve, for example. Preferably, only one surgical opening is made within the thoracic cavity of the patient. However, a thoracoscope may be employed, requiring multiple surgical openings in the patient's thoracic cavity. Additionally, one or more peripheral percutaneous openings (e.g., in the patient's groin) may be employed if necessary for a particular catheter-based method.

If a MIDCAB procedure is performed, a single minimal thoracotomy is preferable as it provides a surgical window sufficient to accommodate surgical instruments for the MIDCAB as well as catheters and other instruments (i.e., cannula, trocar, guide wire, probes, etc.) for carrying out revascularization. Minimally invasive openings (i.e., those having an incision length not substantially more than 12 cm, preferably less than 12 cm, and most preferably less than 10 cm) are preferable; however, larger incisions may be employed if necessary. As between a minimal thoracotomy and multiple port-like percutaneous openings which require the physician to perform the surgery with a thoracoscope and possibly a separate light source, a minimal thoracotomy is preferable because of the greater visibility and accessibility provided by it. The minimal thoracotomy incision may be intercostal or parasternal but is preferably performed intercostally, and preferably on the second, third, fourth, or fifth intercostal spaces, and most preferably on the fourth or fifth intercostal spaces. If employed, multiple percutaneous ports may be formed on either the left or right side of the patient's thoracic cavity, however, the exact locations are dependent upon the above enumerated factors. The means for creating these ports are commonly known in the art of cardiac surgery.

In the case where a minimal thoracotomy is used, and particularly when one or more bypass grafts are contemplated, the surgery is preferably performed in part by means of the Minimally Invasive Direct Coronary Artery Bypass (MIDCAB™) method and system as described in Applicant's copending patent applications having Ser. No. 08/419,991, mentioned above, and Ser. Nos. 08/603,758, 08/604,161, and 08/619,903 which are hereby incorporated by reference in their entirety. The MIDCAB system is comprised of surgical instruments designed to provide atraumatic attenuation of heart motion during cardiothoracic surgery and, therefore, is ideal for cardiothoracic surgeries when the patient is not on CPB. More specifically, the MIDCAB system is used to spread the ribs, providing access to the thoracic cavity, retract the skin from the surgical incision, dampen the movement of the beating heart, and isolate and present the target cardiac vasculature.

Figure 1B:
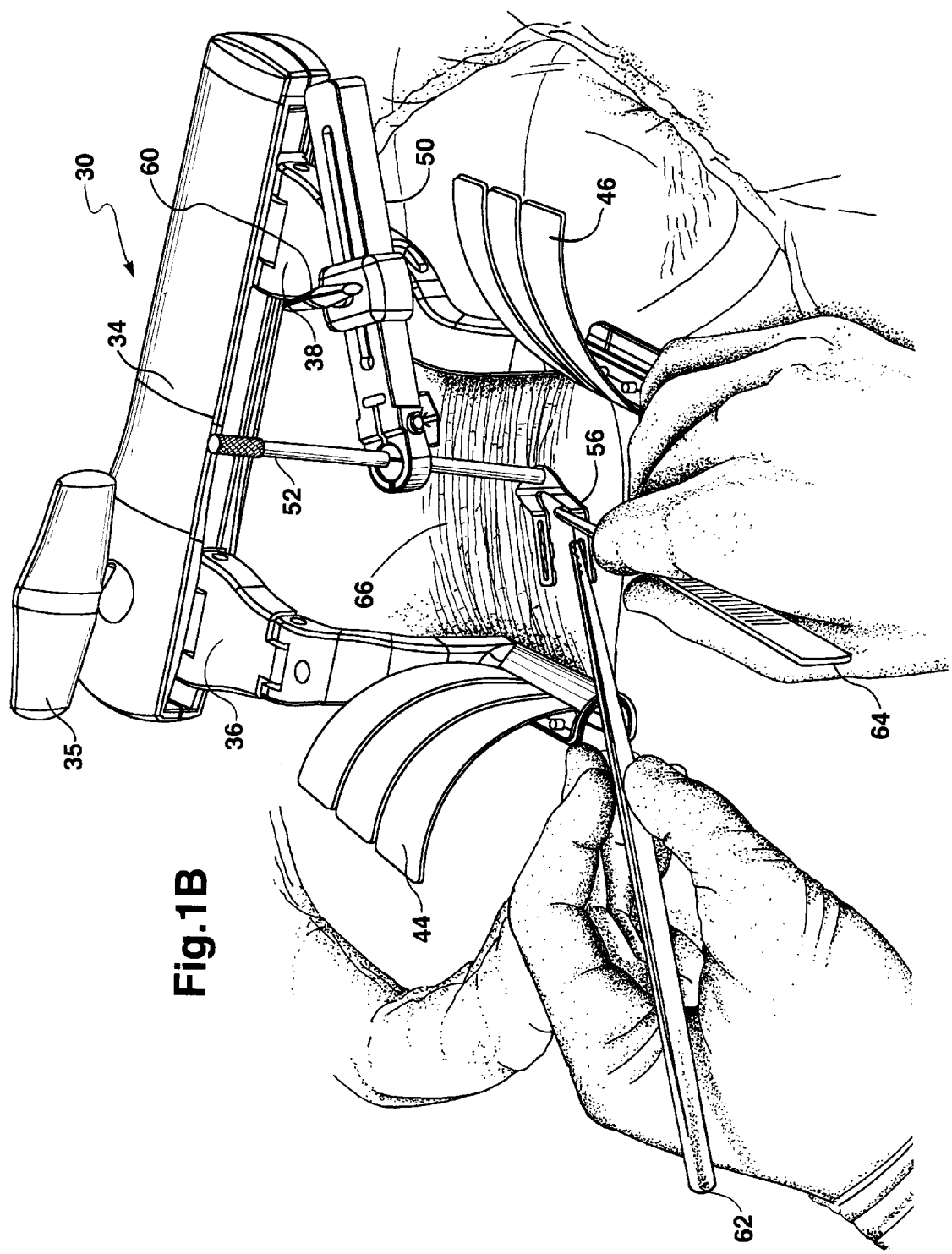
FIG. 1B is a perspective view of the device of FIG. 1A positioned in the thoracic cavity of a patient for its intended application.

A MIDCAB device 30 is illustrated in FIGS. 1A and 1B with FIG. 1B showing the device within a patient's thoracic cavity functioning in its intended application. In general, MIDCAB device 30 includes access platform 32 and stabilizer 48. Access platform 32 in turn includes a spreader 34 having a housing and a spreader knob 35. Extending from spreader 34 is a stationary retractor arm 36 and a moveable retractor arm 38. Enclosed in the housing of spreader 34 is a cable drive mechanism (not shown) which is operated by rotating spreader knob 35, which can accommodate about 50 lbs/in$^2$ or more of torque. This cable drive mechanism laterally translates retractor arm 38 away from retractor arm 36. The operation of spreader knob 35 with spreader 34 may alternatively comprise other suitable configurations such as a rack and pinion mechanism.

Retractor arms 36 and 38 each have two joints 33 having an axial rotation of about 40° for optimal adjustment of arms 36 and 38 when in operation. Attached to the distal ends of retractor arms 36 and 38 are retractor blades 40 and 42, respectively. Blades 40 and 42 are designed to be positioned within an incised intercostal space and have recessed throats 41 and 43 to engage with the rib adjacent thereto. Extending from blades 40 and 42 are a set of skin retractor fingers 44 and 46, respectively.

Stabilizer 48 comprises a stabilizer arm 50 which is slideably mountable to either retractor arm 36 or 38. At the distal end of stabilizer arm 50 is a stabilizer shaft 52 which is in omnidirectional communication with stabilizer arm 50 by means of a ball and socket mechanism 54. Stabilizer arm 50 is adjustably fixed 61 to a retractor arm by stabilizer knob or wing nut 60 and clamp 61. Such a configuration allows liberal positioning of stabilizer shaft 52 within the planar area between retractor arms 36 and 38. The distal end of stabilizer shaft 52 has a stabilizer foot 56 having tines 58 which have a surface designed to atraumatically grip the epicardium of the heart.

MIDCAB device 30 may also include other optional accessories (not shown) which are mountable or attachable to either access platform 34 or stabilizer 48. Such accessories include but are not limited to a scope, a light, an arterial graft holder, and a suture holder.

MIDCAB device 30 is employed as follows: in an initially collapsed state, the device 30 is placed over the incision with retractor arms 36 and 38 positioned intercostally between opposing ribs which are proximal to the chest incision. After retractor blades 40 and 42 are engaged with the ribs, skin retractor fingers 44 and 46 are to be bent away from each other over the patient's skin to displace soft tissue away from the incision. Spreader knob 35 can then be rotated to displace moveable retractor arm 38 in a lateral direction away from stationary retractor arm 36 causing the ribs to spread laterally and displace vertically with respect to each other.

Once the desired opening size is achieved, the physician can proceed with the revascularization procedures. With respect to a MIDCAB procedure, after access has been established, an arterial blood source is then prepared for subsequent bypass connection to the narrowed coronary artery to be bypassed at a location beyond the narrowing. The arterial blood source may be supplied by either an existing artery, such as the left internal mammary artery (LAMA), or by shunting a natural or synthetic blood vessel, typically a length of the saphenous vein, from the aorta to the target vessel. However, it is preferable to use a peticled or transected arterial conduit, such as the LIMA, the right anterior descending artery (RIMA), or the gastroepiploic artery as they tend to have a better patency rate and require only one anastomosis. When an existing artery is used as the graft vessel, it is preferably harvested from its natural location by means identified in the above-identified patent applications which have been incorporated by reference.

After the graft vessel is harvested and prepared for the anastomosis, the target site of the coronary artery to be bypassed is identified. Most typically, the diseased coronary artery which is the subject of the bypass is the LAD, however, the methods of the present invention are suitable for bypassing other arteries including the right coronary artery (RCA), the obtuse marginal artery, the ramus intermedius artery, and the posterior descending artery, among others.

Stabilizer arm 50 with the attached stabilizer shaft 52 is then connected to either retractor arm 36 or 38 depending on the physician's preference. Stabilizer shaft 52 is then positioned above the target coronary artery to be bypassed and carefully lowered to the epicardium. Incremental pressure is applied to the epicardium until the desired stabilization of the heart is achieved, i.e., until the contraction of the heart does not cause either vertical or horizontal motion at the target site. Stabilizer shaft 52 is then locked into place by turning stabilizer knob 60. Optimal stabilization of the epicardium is achieved when the vessel between tines 58 of stabilizer foot 56 is stable relative to the heart's motion. At this point, the anastomosis is performed between the graft vessel and the target vessel by various means commonly known in the art of cardiac surgery. FIG. 1B is a perspective view of the MIDCAB device of FIG. 1A in application in a patient's thoracic cavity 66. Here, a physician is shown performing the anastomosis with surgical instruments 62 and 64 while movement of the patient's heart is being stabilized by stabilizer foot 56.

Catheterization may now be performed either directly through the minimal thoracotomy, or through peripheral percutaneous openings, or both. For purposes of this description, intraoperative catheterization is described as being performed through the minimal thoracotomy wherein catheters are directly inserted into the coronary artery system via a cannula which is to be introduced into the wall of the patient's aorta. However, percutaneous insertions sites (e.g., the groin area) and other coronary lumen entry sites (e.g., the femoral artery, subclavian artery, left subdlavian artery, etc.) are contemplated. For example, based on the clinical diagnosis, it may be determined that cannulation of the subclavian artery is preferential to cannulation of the aorta. As the subdlavian artery may be more difficult to access (for purposes of cannulation) than the aorta from a minimal thoracotomy in the fourth or fifth intercostal space, a percutaneous opening through the chest wall directly above the subdlavian artery and superior to the minimal thoracotomy opening may be required for cannulation of the subdlavian artery.

Prior to commencing intraoperative catheterization (in the context of the minimal thoracotomy described above, with or without a MIDCAB procedure), it may be necessary to optimize visualization of and access to the aorta. This necessity may arise when access is made at a location in the thoracic cavity which is below the fourth intercostal space. This may involve readjusting the access platform component 32 or utilizing another retractor or rib pry-bar (as disclosed in Applicant's patent applications having Ser. Nos. 08/604, 161 and 08/619,903) to further offset the rib cage. After having established adequate access to and visibility of the aorta (whether through a minimal thoracotomy or through one or more percutaneous ports), the physician is ready to cannulate the aorta.

Figure 2:
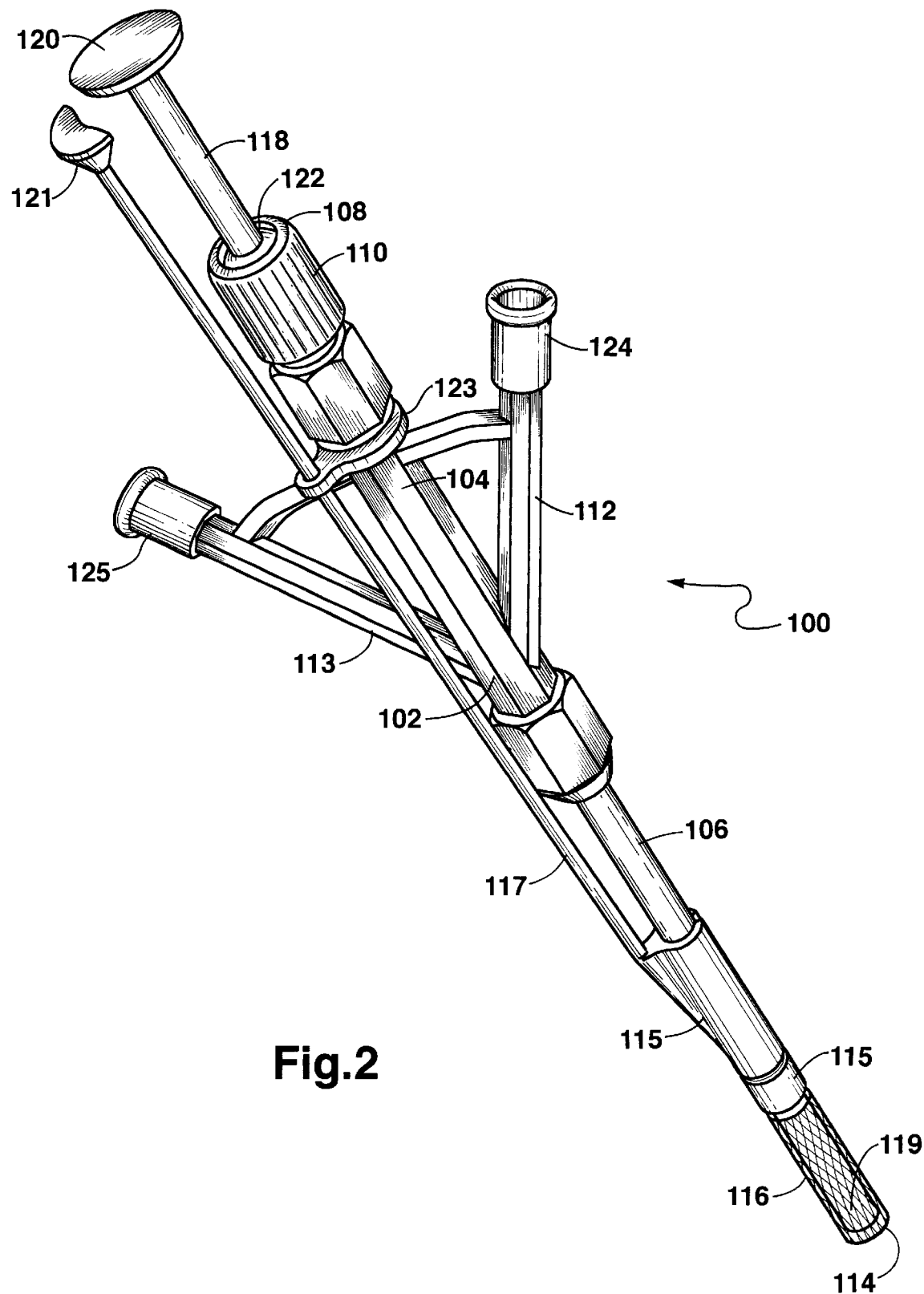
FIG. 2 is a schematic side view of one embodiment of the arterial access device of the present invention.

Cannulation of the aorta or other appropriate coronary lumen is accomplished with the present invention by means of an arterial access device 100 of FIG. 2. Access device 100 has a tubular body or cannula 102 having a top portion 104 and a shaft portion 106 and housing a central lumen. Cannula 102 is preferably relatively small in size and may be rigid or flexible. Cannula 102 may be made of a metal, plastic, polyurethane, polyethylene, polycarbonate, nylon or other similar materials suitable for medical applications. Extending upwardly at an angle from top portion 104 are two auxiliary tubular arms or ports 112 and 113 each having a central lumen which is in fluid communication with the central lumen of cannula 102. Although two arms are shown, none are required and any number of arms are contemplated within the scope of the present invention. The purpose and function of such auxiliary arm(s) is discussed in more detail below with respect to FIG. 5. At the proximal end 108 of cannula 102 is a valve mechanism 110 which prevents blood from flowing out of end 108 and allows insertion of a trocar or catheter without leakage. Valve mechanism 110 is preferably a rotating hemostatic valve or Luer fitting which selectively seals or provides access to the central lumen. Such valves or fittings are commonly used in the art of cannulation and catheterization. Other valve mechanisms which are suitable for such an application may also be used with the present invention. When closed, valve mechanism 110 seals port 122 closed. Also illustrated but optional, are valve mechanisms 124 and 125 at the opening of arms 112 and 113, respectively. Valve mechanisms 124 and 125 function similarly to valve mechanism 110. The distal end of cannula 102 comprises an atraumatic tip 114 which is made of a compliant plastic or other similar material. Tip 114 preferably has a smooth shape so as not to damage the tissue upon entering the aortic wall. Also, tip 114 is preferably radially expandable upon entering the aortic wall or has a width which is slightly greater than that of shaft 106 so as to anchor cannula 102 within the aortic wall.

Positioned concentrically within cannula 102 is a trocar or introducer device 118 (partially shown in phantom) having a tapered body which ends distally in a very sharp point 119 (shown in phantom) and having a head 120 at the proximal end. Head 120 has a dimension such that it sealingly engages with port 122. Trocar 118 is relatively rigid and may be made of materials (listed above) similar to those used for cannula 102. Cannula 102 has a length not substantially greater than about 30 cm, and trocar 118 has a length such that it extends beyond the end of atraumatic tip 114. The specific length of cannula 102 and trocar 118 are dependent upon the coronary lumen being cannulated. Cannula 102 has an internal diameter of not substantially more than 5 French and preferably less than 5 French, and trocar 118 has an external diameter such that it is slideably moveable within cannula 102. It is preferable that the arterial access device of the present invention, and particularly the diameters of cannula 102 and trocar 118, have relatively small profiles to ensure a small puncture site in order to reduce trauma to the coronary lumen and to minimize the possibility of extricating plaque that has formed on the interior of the lumen.

Positioned concentrically around the distal end of cannula 102 is a sealing member 116 and a sleeve 115. Sealing member 116 may be an expandable sheath, such as a coated metal braid, an inflatable balloon, or other similar means, which sealingly engages with an arterial wall when operably positioned therein (see FIGS. 3A–C). Sealing member 116 is shown as expandable braid having its distal end connected to the tip of cannula 102. Extending from the proximal end of sleeve 115 is elongated arm 117 which runs approximately parallel cannula 102. In the case of a balloon type sealing member, actuating lever is in the form of a syringe for inflation and deflation of the balloon. A clip 123 serves to maintain elongated arm 117 in a parallel relationship with cannula 102. Mounted at the proximal end of elongated arm 117 is head 121. Actuating member 115 is slideably moveable along the length of cannula 130 to actuate expansion of braid 132. Alternatively, sealing member 116 may comprise a flexible flange or other similar mechanism which is flexible enough to atraumatically enter the entry site and then automatically radially expand upon entry into a coronary lumen without the need for an actuating means.

FIGS. 3A–C illustrate the operation of the sealing member of the arterial access device of FIG. 2 upon insertion into a coronary lumen, such as the aorta. Cross-sectional views are provided of the distal portion of a cannula 130, a trocar 134, braid 132 having a constricted portion 133, and sleeve 131 of an arterial access device of the present invention. FIG. 3A illustrates trocar 134 puncturing lumen wall 140 in the direction of arrow 142. Cannula 130 is introduced into lumen wall 140 with atraumatic tip 136 snugly passing through the puncture site and until constricted portion 133 of braid 132 reaches the edges of lumen wall 140 (FIG. 3B). Sleeve 131 is then pushed downward, in the direction of arrow 144, compressing braid 132 and causing braid 132 to expand radially as the ends thereof are axially moved closer together wherein the portions of braid 132 above and below artery wall 140 are caused to expand radially outward to seal the entry site (FIG. 3C). Trocar 134 can then be removed from cannula 130 in the direction of arrow 146. Although braid 132 is illustrated as having expanded portions above and below artery wall 140, other embodiments which provide expansion either above or below artery wall 140 are contemplated.

Figure 4C:
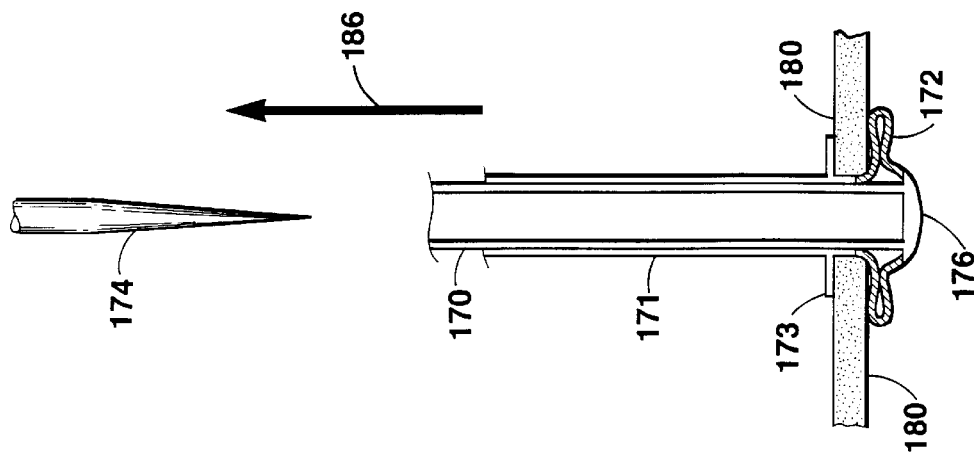
FIGS. 4A–C are schematic representations depicting the operation of another embodiment of the arterial access device of the present invention upon insertion into a coronary lumen of a patient.
Figure 4B:
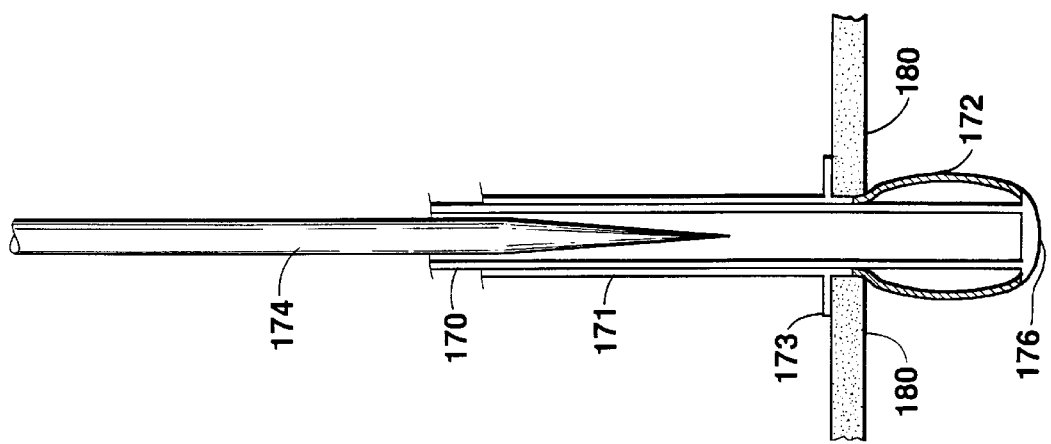
Figure 4A:
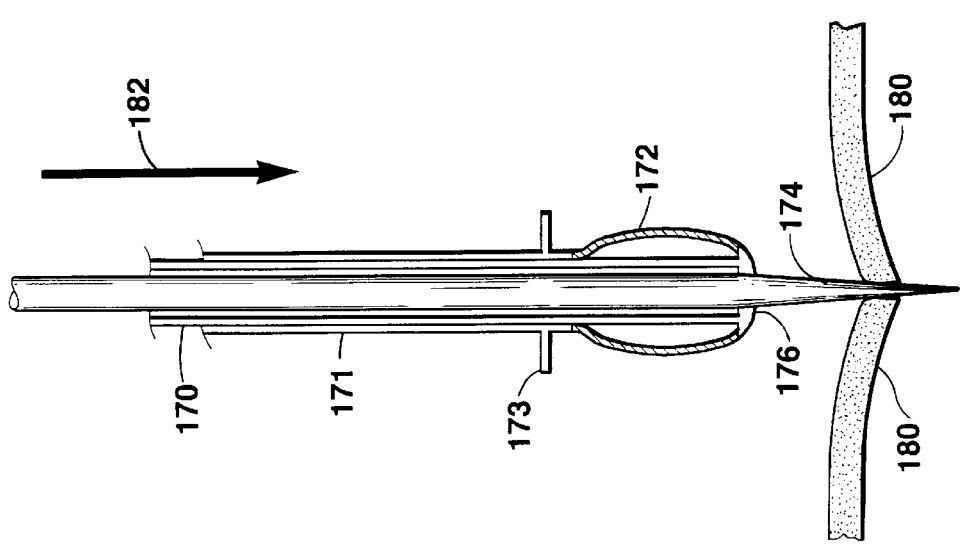

FIGS. 4A–C illustrate similar cross-sectional views of the operational steps involved in the insertion of another embodiment of the arterial access device of the present invention having a cannula 170, a trocar 174, a braid 172, and a sleeve 171. Sleeve 171 is provided with a stop member 173 which is extends radially from the distal end of sleeve member 171. The distal end of braid 172 is attached to tip 176 and the proximal end of braid 172 is attached to stop member 173. FIG. 4A illustrates trocar 174 puncturing lumen wall 180 in the direction of arrow 182. Cannula 170 is introduced into lumen wall 180 until stop member 173 abuts the exterior of lumen wall 180 (FIG. 4B). Cannula 170 is then pulled upward, in the direction of arrow 184, compressing braid 172 and causing braid 172 to expand radially outward within lumen wall 140 to seal the entry site (FIG. 4C).

Figure 5:
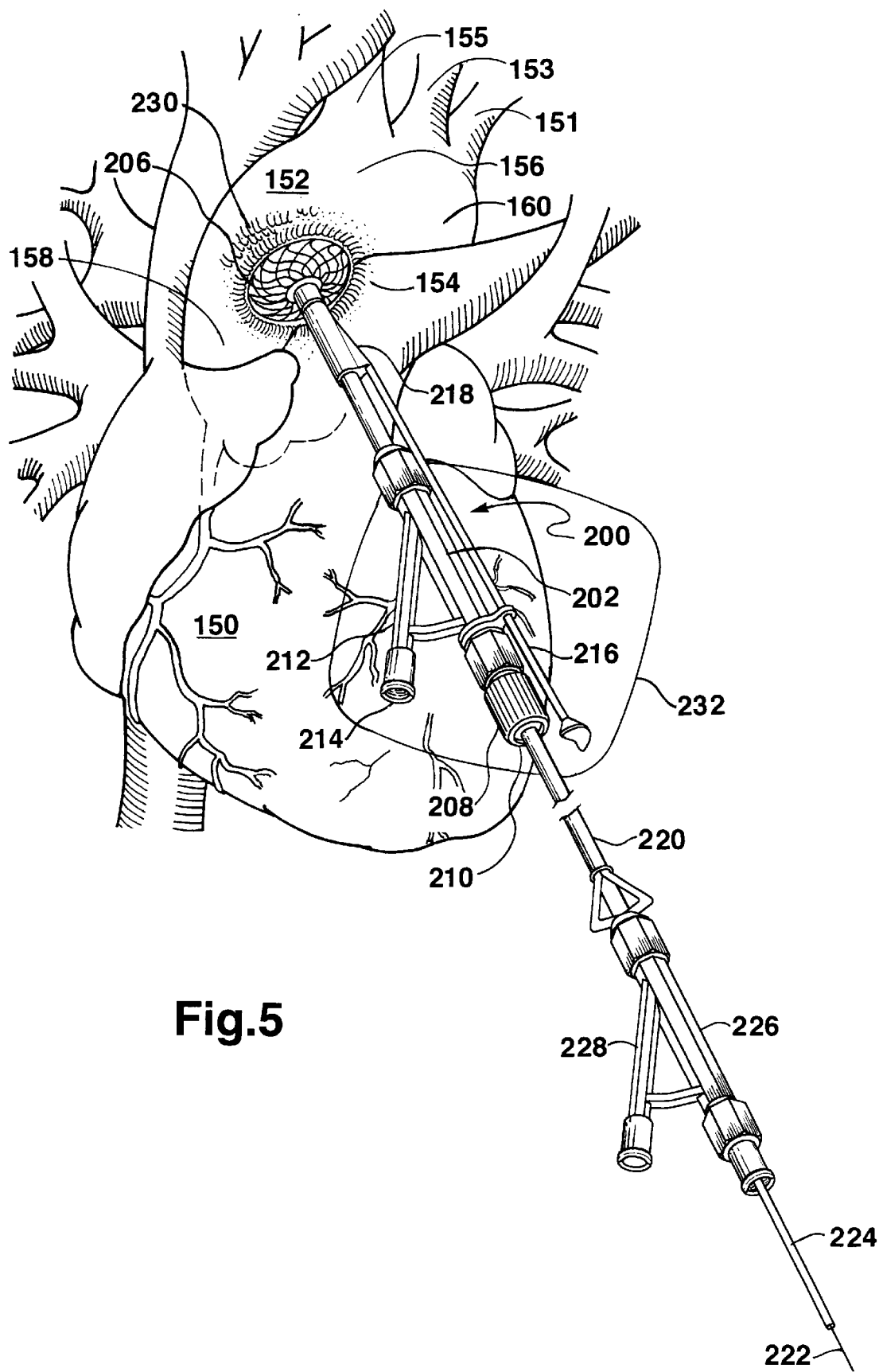
FIG. 5 is a schematic illustration of the anterior view of a human heart with one embodiment of the arterial access device and intraoperative catheters of the present invention positioned in the aorta.

Returning to a description of the revascularization procedures of the present invention and referring now to FIG. 5, there is shown an access device 200 of the present invention which has been inserted into the aorta 152 of heart 150. The entry site or location of the cannulation may be in any appropriate location within the coronary arterial system, preferably in the aorta 152 or an artery branching from the aorta 152, such as the subdlavian artery 151, the left common carotid artery 153, and the brachiocephalic trunk (innominate artery) 155, and most preferably in either the aortic arch 156, the ascending aorta 158, or the descending aorta 160.

Prior to commencing cannulation, it is preferable to provide a purse string suture configuration 230 in the wall of aorta 152 at the intended entry site which approximates the shape and size of the cannula 202. Such a suture configuration 230 can be used to minimize the leakage of blood at entry site 154 upon removal of cannula 202. This step may alternatively be performed after insertion of cannula 202 into aorta 152. Other means known in the art, such as an occlusion cuff, may also be used to create an atraumatic seal at the entry site.

The physician commences cannulation of aorta 152 by introducing access device 200 through the MIDCAB window 232 (shown as a schematic outline only) and into the aortic wall to create an entry site 154. The physician then punctures the aortic wall with the sharp tip of trocar 201 (not shown) and continues to insert cannula 202 into the wall of the aorta 152 at entry site 154 until braid 206 engages the aortic wall, as shown in FIGS. 3A–B. Actuating lever 216 is then pushed to compress sleeve 218 against braid 206 to seal the aortic wall to cannula 202, as shown in FIG. 3C. After forming entry site 154, trocar 201 is pulled from cannula 202, leaving cannula 202 anchored and sealed within the aortic wall by means of the braid 206. Valve mechanism 208 is then closed to prevent the back flow of blood (and any other fluids, such as drugs, which may be infused into the patient's coronary artery system) from port 210. Aortic access device 200 is provided with one auxiliary side arm 212 having valve mechanism 214 communicating therewith. It is preferable that auxiliary valve mechanisms, such as valve mechanism 214, are properly closed prior to introduction of device 200 into the aorta 152 in order to prevent the back flow of blood through arm 212.

At this point, the physician is ready to begin intraoperative catheterization by introducing a guide catheter 220 into port 210 of cannula 202. Guide catheter 220 may have an adapter 226 which is sealably removably mounted to the proximal end guide catheter 220 for receiving therapeutic or diagnostic catheters to be guided to selected target sites within the coronary arterial network. Adapter 226 has a central lumen in fluid communication with guide catheter 220 and may have a structure similar to the top portion of cannula 202. For example, adapter 226 may include an auxiliary arm 228 for receiving additional catheters or elongated surgical instruments, or contrast material when a catheter-based fluoroscopy procedure is employed.

Figure 6:
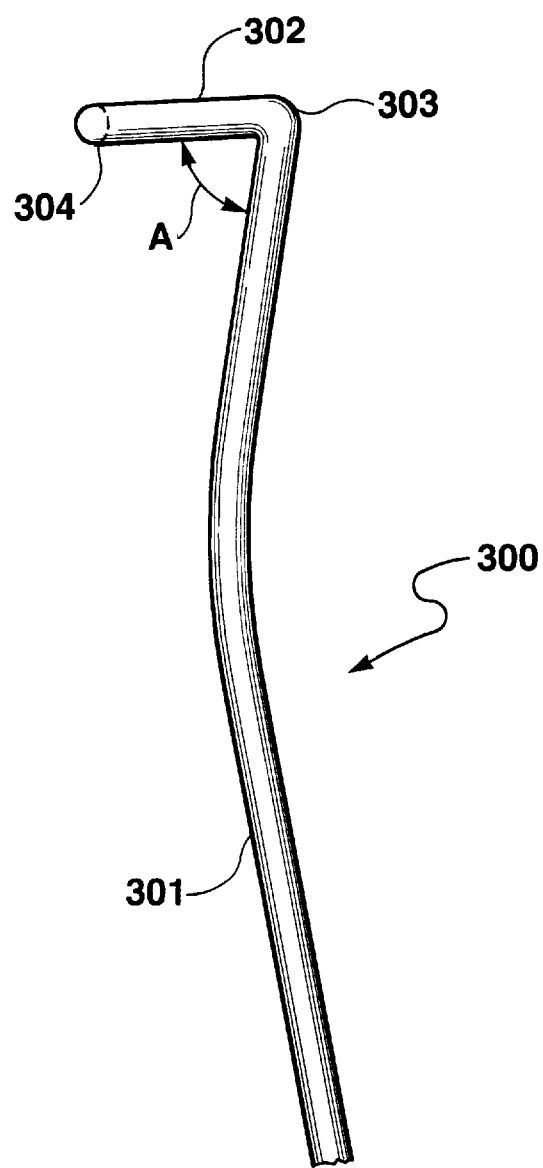
FIG. 6 is a schematic illustration of an embodiment of a guide catheter of the present invention.

The use of guide catheters and guide assemblies (i.e., guide catheter and guide wire combinations) for catheterization is commonly known in the art of cardiac intervention; however, such guide assemblies are primarily designed for peripheral percutaneous insertion through the femoral artery. Accordingly, they are likely to be too long and not properly shaped for central cannulation. For use with the methods and devices of the present invention, it is preferable to use a guide catheter 300, as shown in FIG. 6, which is adapted and has a shape for insertion directly through the aorta or other suitable coronary lumen and into a selected branch artery ostium. Guide catheter 300 is flexible and comprised of materials commonly used in the art of catheters, and is shown having a shaft 301, a tip portion 302, and a profiled portion 303. At the distal end of tip portion 302 is a tapered atraumatic tip 304 which is preferably made of a compliant polymer. Between the distal end of shaft 301 and the proximal end of tip portion 302 is profiled portion 303 comprised of a bend. The angle A of bend 303 is between about 20° and 90°, but may be greater or smaller depending on the location of the ostium of the coronary artery to be treated and whether the catheterization is done intraoperatively or transluminally. The length of shaft 301 is not substantially greater than 50 cm, and preferably closer to 40 cm. The length of tip portion 302 is preferably between about 5–10 cm, but may be more or less depending on the location of the ostium of the coronary artery being treated.

The guide catheter design of FIG. 6 allows the distal end of guide catheter 300 to be inserted directly through the wall of the aorta, and preferably through the cannula of the aortic access device discussed above, and become positioned either inside or adjacent the ostium of the desired coronary artery to be revascularized. Additionally, such a guide catheter 300 is less likely to be unseated and will enable therapeutic and diagnostic catheters to reach very distal and tortuous coronary anatomy. It is also preferable that guide catheter 300 have other characteristics, which are well known in the medical community, for providing a high degree of direction control for placing other therapeutic and diagnostic catheters. Such characteristics include high torque transmission for engagement, high inner lumen lubricity to facilitate insertion of secondary devices, low kinking characteristic, good tip memory, and a smooth distal leading surface to prevent damage to the vasculature. Additionally, it is preferable to provide an imaging element or radiopaque marker at the distal tip of the guide catheter to enhance its visibility should a fluoroscope be used. Optionally, a structural element, such as a balloon, may be employed for anchoring and/or sealing the guide catheter within the coronary anatomy. An example of such a guide catheter is disclosed in U.S. Pat. No. 5,451,207 which is hereby incorporated by reference.

Returning to a description of FIG. 5 and to a description of the intraoperative catheterization procedure, guide catheter 220 is inserted until its tip (not shown) is positioned at the ostium of the coronary artery to be treated (not shown). Insertion of guide catheter 220 is then followed by insertion of a guide wire 222 into guide catheter 220 via adapter 226. The tip of guide wire 222 is then delivered through aorta 152 to the selected coronary artery ostium (not shown). After insertion of guide wire 222, it is steered to the target site(s) or lesion(s) within the selected coronary artery by means commonly known in the art, such as fluoroscopy, angioscopy, or intravascular ultrasound. To this end, arm 212 which, extends from cannula 202, may be used to receive the distal end of a syringe (not shown) for injecting contrast material. A therapeutic or diagnostic catheter 224 or other elongated surgical instrument, such as a coronary probe, is thenr disposed within guide catheter 220 and advanced over guide wire 222 to the target site. The intended diagnosis or therapy is then performed at the target site.

It is intended that catheter 224 or other elongated surgical instrument used, in the context of a central cannulation of the coronary anatomy, have a profile and length that are practical for use with the guide catheter and the guide wire assembly of the present invention. It will also be appreciated that a variety of therapeutic and diagnostic approaches and catheter designs may be used with the catheter methods (both those done under direct vision and those involving peripheral insertion of catheters) of the present invention. Catheter-based therapies which may be used in the context of the present invention include but are not limited to angioplasty, stent placement, ablation, and drug delivery. Additionally, a variety of diagnostic catheter techniques may be employed with the methods of the present invention. Such diagnostic techniques include; for example, fluoroscopy, radiography, angiography, endoscopic imaging, and ultrasonic imaging. There are still other techniques which provide both therapeutic treatment and diagnosis contemporaneously using the same catheter assembly.

Several of these therapeutic and diagnostic techniques and catheter designs are described, for example, in U.S. Pat. No. 5,084,010 which is hereby incorporated by reference in its entirety. That patent discloses a catheter system having interchangeable components which are structurally and functionally distinct so that different catheter configurations may be constructed by a treating physician immediately before and/or during therapeutic and diagnostic catheter procedures. The catheter system includes a flexible catheter tube having an open cylindrical housing, and a variety of interchangeable interventional components such as cutting elements for cutting away at the atheroma and a vacuum element for aspirating the atheroma material. The catheter system also comprises and internal drive member capable of rotational and axial translation of the interventional components.

Other exemplary catheter systems, and particularly ablation catheters, are disclosed in U.S. Pat. Nos. 5,402,790, 5,507,292, and 5,569,276, which are hereby incorporated by reference in their entireties. These patents disclose a catheter having a head for abrading stenotic material and an aspirator within the catheter housing to flush out abraded material from the patient's body. An imaging means is also provided for viewing the stenosis and ablation process.

A similar ablation catheter is disclosed in U.S. Pat. No. 5,395,311, which is also hereby incorporated by reference in its entirety. The catheter includes a variably expandable cutter mechanism which provides for incremental expansion of the cutter head with each consecutive pass through an arterial blockage. Biologically active compounds are bound to the catheter tubing or an expandable balloon circumferentially situated, and are brought into contact with freshly cut tissues at the blockage site to promote healing and inhibit regrowth of the blockage. Alternatively, a catheter is provided with two balloons which are positioned to straddle the cut tissue, and then inflated. Biologic agents are then flushed through the space between the balloons. Still another embodiment provides a stent having biologic agents bonded thereto and which is permanently implanted at the site of the ablated blockage.

In addition to ablation catheters which employ cutting elements, other ablation catheters utilize a laser, RF, or microwave energy source. An example of laser ablation is found in U.S. Pat. No. 5,290,275 which is hereby incorporated by reference in its entirety. A laser ablation system is disclosed which includes a catheter having optical fibers mounted therein to provide controlled delivery of a laser beam for percutaneous intravascular treatment of atherosclertotic lesions. A computer controlled system automatically aligns selected optical fibers with the laser and controls exposure time. The catheter is also provided with a transparent protective shield at tits distal end for mechanically displacing blood and for protecting the fibers. Spectroscopic diagnostics are employed to determine the accuracy and extent of tissue removal.

An example of an ablation system utilizing ultrasonic energy is found in U.S. Pat. No. 4,870,953, which is hereby incorporated by reference. Disclosed is a flexible wire probe having a bulbous tip and which is carried in an intravascular catheter. The probe is coupled to an ultrasonic energy source such that when the tip is placed in contact with an intravascular blockage, the probe carries ultrasonic energy to the blockage. The flexible probe is made to vibrate transversely as well as forward and backward to maximize ablation of the blockage.

A multipurpose ablation system is disclosed in U.S. Pat. No. 5,500,012, hereby incorporated by reference in its entirety. The system provides a mapping-guiding catheter which can be utilized with any ablation catheter for mapping a specific myocardial tissue and for guiding an ablation catheter to the target site. An ablation catheter is also disclosed which monitors heart rate and tissue properties, such as temperature and electrical characteristics.

Examples of dilation catheters and angioplasty procedures for use in performing the methods of the present invention are found in U.S. Pat. Nos. 4,976,720, 5,087,247, 5,196,024, 5,411,016, and 5,542,925 which are hereby incorporated by reference in their entireties. U.S. Pat. No. 4,976,720 discloses a very low-profile dilation catheter formed of a thin-walled tubing such as polyimide and which has an inner lumen diameter of not more than 0.076 mm greater than the diameter of a guide wire disposed therein. Another relatively low profile angioplasty balloon catheter, disclosed in U.S. Pat. No. 5,087,247, is provided for low pressure, sustained inflation angioplasty. Such a design and method minimizes arterial dissection or tearing at the lesion, and facilitates healing. U.S. Pat. No. 5,196,024 discloses another angioplasty balloon in which the angioplasty balloon is provided with sharp cutting edges situated longitudinally along the balloon for making corresponding cuts in the vessel wall. The cuts increase the diameter of the vessel and thereby decreases the subsequent secondary cellular proliferation or restenosis in the vessel wall. U.S. Pat. No. 5,411,016 discloses a balloon dilation catheter which includes a long shaft where the distal portion of the shaft within the balloon is optically transparent. This optically transparent section allows an angioscope to visualize the treatment site of the artery while balloon dilation is in progress. U.S. Pat. No. 5,542,925 discloses a perfusion type balloon dilation catheter which precludes excursion of a guide wire through a perfusion port when the guide wire is advance through the interior of the catheter.

The hybrid methods of the present invention also include stent delivery applications. Examples of suitable stent delivery catheters and procedures are disclosed in U.S. Pat. Nos. 4,768,507, 5,344,426, and 5,545,135, which hereby incorporated by reference in their entireties. In U.S. Pat. No. 4,768,507 a PTCA catheter is provided which employs and transluminally places a biocompatible, non-thrombogenic coil spring stent. The stent is designed to have an unrestrained diameter between 1.1. to 5.0 times larger than the diameter of the catheter core within which it is stored prior to insertion. Another example of a stent placement catheter suitable for use with the present invention is disclosed in U.S. Pat. No. 5,344,426. The catheter of that application delivers an expandable stent to a target site within an artery, fixes the stent in an expanded condition within the artery, and then is immediately removed, leaving the stent in place. U.S. Pat. No. 5,545,135 discloses another perfusion balloon stent which is inserted into a coronary artery following a PTCA procedure.

The delivery of drugs, other therapeutic agents, and biologic material by means of intravascular catheters are also commonly known in the art and have application with the hybrid method of the present invention. Examples of such catheter systems are disclosed in U.S. Pat. Nos. 5,112, 305, 5,411,466, 5,460,610, 5,514,092, 5,423,744, which are hereby incorporated by reference.

In particular, a catheter system and method for precisely delivering therapeutic agents at a selected intravascular location is disclosed in U.S. Pat. No. 5,112,305. That invention employs a double lumen catheter that has tubular extensions projecting at various angles from the outer surface of the catheter. Therapeutic agents are released through these tubular extensions to provide high local concentrations of otherwise toxic agents to the deeper layers of the vessel wall for reducing the incidence of late restenosis attributed to cellular hyperplasia. U.S. Pat. No. 5,411,466 discloses a method and a catheter-like device for treatment of the stenosed region of an artery after reduction of the region by angioplasty by applying a radioactive dose to the region. The radioactive dose may be a solid, liquid, or gaseous form of materials such as Radon, Gold, or Radium, among others. Another catheter-based system, disclosed in U.S. Pat. No. 5,460,610, provides a catheter having two balloons for performing a combination of balloon angioplasty and chemoplasty of vascular region which has been dilated, without requiring withdrawal of the catheter and insertion of a different catheter. In U.S. Pat. No. 5,514,092, various catheter embodiments are disclosed for drug delivery or for both dilation and drug delivery. In one embodiment, drug delivery ports are provided between occlusion balloons. In another embodiment, a dilation balloon is also provided between the occlusion balloons. In yet another embodiment, a double layered balloon is provided to simultaneously dilate the stenosed area and deliver medication to the area. An example of a catheter system for dispensing biologic agents intravascularly is disclosed in U.S. Pat. No. 5,423,744 in the form of an endothelial deployment catheter. The catheter is a multi-zone, multi-lumen device that interfaces a plurality of input-output peripherals proximally and provides working zones distally. The working zones include a pair of spaced fluid inflatable balloons which flank a controlled electrically charged mediated dispersion zone. The dispersion zone includes a dispersion chamber in contact with an electrode and having a plurality of openings through which endothelial cell culture can be discharged into the vascular segment between the spaced balloons.

Surgical instruments other than catheters are also suitable for therapeutic purposes for use with the hybrid methods of the present invention. In particular, the rotational angioplasty system or "Rotablatorm" described in U.S. Pat. No. 5,314,407 is commonly known in the art and is incorporated herein in its entirety. The Rotablator comprises a gas driven prime mover having an integrated water pump and fiberoptic tachometer. The prime mover is connected, via a hollow helical drive assembly, to an ellipsoidal, rotating, abrasive burr which is used to recannulate the patient's artery. The burr is provided with a central opening therethrough which permits the burr and drive assembly to be threaded over a guide wire.

As mentioned above, catheter-based diagnostic and catheter positioning applications are also within the scope of the hybrid revascularization methods of the present invention. Some examples of diagnostic catheters and catheter-based methods are found in U.S. Pat. Nos. 4,973,306, 4,935,017, 5,038,789, 5,269,326, 5,485,840, and 5,313,949 which are hereby incorporated by reference in their entirety. U.S. Pat. No. 4,973,306 discloses an angiographic catheter for the selective angiography of the right coronary artery. The catheter has a preformed curvature for insertion into the aortic arch and having a soft tip oriented such that it is disposed above the ostium of the right coronary artery when the catheter is disposed within the aortic arch. The catheter also has a lumen extending through it for the injection of angiographic dye therethrough to the right coronary artery. Another catheter assembly and method for catheterization relevant for angiography procedures is disclosed in U.S. Pat. No. 4,935,017. The catheter of that invention has a means by which the curved configuration at the distal portion of a catheter can be varied while the catheter remains in the patient, thereby enabling a change in catheter shape without requiring catheter exchanges. Such a system enables right and left coronary angiographic procedures to be performed without changing catheters.

A method and Dopplar transceiver device used for diagnostic purposes as well as for the retrograde steering a catheter to a desired site within the coronary anatomy is disclosed in U.S. Pat. No. 5,038,789. More particularly, a catheter is provided with a first lumen which is capped at its tip with a Doppler-type ultrasound transceiving crystal. A second lumen is hollow and at its proximal end is provided with a connector which allows the attachment of a variety of instruments, such as a manometric device for obtaining measurements of blood pressure at the catheter tip or a syringe for the injection of contrast media or therapeutic compounds. A Doppler ultrasound control apparatus is also provided to serve as a power supply for the transceiver and to receive and process signals produced by the transceiver. Another ultrasonic imaging apparatus for use in an atherectomy method is disclosed in U.S. Pat. No. 5,485,840. This patent discloses a directional atherectomy catheter is provided with a cutter which has a marker visualizable on fluoroscopy, and used with an ultrasonic imaging apparatus to select the cutter size. Yet another ultrasound imaging method and apparatus are disclosed in U.S. Pat. No. 5,313,949. This method provides for imaging the interior of blood vessels which includes scanning an ultrasonic signal in a preselected pattern about the interior of the vessel. This is accomplished by an ultrasonic transducer positioned at the distal end of a catheter. A receiver is provided for receiving signals from the ultrasonic transducer, the signals providing two-dimensional images of interior anatomy of vessels, including any stenosis or occlusion present. Such imaging apparatus and method is combined with interventional therapeutic techniques to reduce vascular stenosis, where the stenosis may be imaged prior to, during, and after intervention.

Catheter-based cardiac procedures other than those specifically directed to coronary revascularization, but which involve diagnosis or treatment of the heart, may also be performed in the context of the hybrid method of the present invention. An example of such a procedure is disclosed in U.S. Pat. No. 5,269,326, which is hereby incorporated by reference in its entirety. Specifically, a method for treating and diagnosing the heart selectively via the pericardial space by means of guiding a catheter downstream through one of the venae cavae to the right atrium. Once inside the right atrium, the catheter is passed into the right auricle. The wall at the apex of the right auricle is then pierced with the catheter, and the catheter is advanced into the pericardial space. This method can be used, for example, to provide electrical stimuli to the heart (e.g., for pacing, cardioversion, and defibrilation), to sense ECG signals, to deliver pharmacologic agents to the heart, to remove pericardial fluid (e.g., for analysis or pericardiocentesis), or to inject a radiolabelled or echo-sensitive dye into the pericardial space for precision fluid imaging.

Although some of the above described exemplary catheter systems and surgical instruments are disclosed for specific application through an incision cite peripheral to the chest cavity or are not otherwise described as insertable into the coronary anatomy under direct vision, it will be appreciated by those skilled in the art that such catheters and instruments can be modified to provide profiles and lengths which are suitable for application in the central cannulation method of the present invention.

Based on pre-operative procedures and tests conducted on the patient, the physician may know, prior to commencing the surgery, the exact location(s) and extent of stenosis or occlusion within the patient's coronary artery system. In which case the physician may initially proceed with one or more therapeutic catheters to treat the target site(s). If, however, diagnostic procedures have not been preoperatively conducted or supplemental diagnosis is believed to be necessary before proceeding to treat the identified target sites, the physician may choose to first employ one or more diagnostic catheters. Typically, a physician may use diagnostic catheters after treatment with therapeutic catheter revascularization in order to determine the patency achieved at the target site(s). Thus, the order in which a physician employs any therapeutic or diagnostic instrument or catheter with the devices and in the course of the methods of the present invention is case-specific, and is not intended to be limited by this description. It is also understood that, in the context of the present invention, one or more types of catheter-based therapies may be employed at one or more target sites within one or more coronary arteries during one revascularization operation. Thus, the number and types of catheter-based therapies is not intended to be limited by this description.

Returning to a discussion of FIG. 5, upon completion of the intraoperative catheterization, all catheters and instruments are removed from cannula 202. The sealing means (not shown) is released or disengaged from its sealed position by pulling up on the actuating means (not shown), and cannula 202 is then removed from the aorta. If a suture, such as purse string suture 230, has been used to constrict the entry site 154, it is now used to pull entry site 154 closed upon removal of cannula 202. Additional suturing or other anstomosis may be provided to close the entry site if necessary.

Following completion of the intraoperative cannulation and any other cardiac intervention conducted, all access, stabilization, anastomosis, and viewing devices, if any, are removed from the thoracic cavity. All surgical openings are sealed in a conventional manner. Finally, the patient is allowed to recover from anesthesia.

Although the methods and devices of the present invention have been described in some detail by way of illustration and example, it will be readily apparent to those skilled in the art that certain modifications and other embodiments may be practiced without departing from the spirit and scope of the invention and which are within the scope of the appended claims.

What is claimed:

1. A method of revascularization of a patient's heart without placing the patient on cardiopulmonary bypass comprising the steps of:

performing at least one coronary artery bypass graft procedure on a beating heart through at least one surgical or percutaneous opening of not substantially more than 12 cm in length in the patient's thoracic cavity;

contemporaneously with said step of performing said coronary artery bypass graft procedure, delivering at least one catheter means through said at least one opening to a target site within a coronary artery for treating or evaluating said target site with said at least one catheter means.

2. The method of claim 1 wherein said at least one catheter means is selected from the group consisting of an angioplasty catheter, a dilation catheter, a stent delivery catheter, an ablation catheter, and an abration catheter.

3. The method of claim 1 wherein said at least one catheter means is selected from the group consisting of a catheter employing laser, radio frequency, microwave, or ultrasonic energy.

4. The method of claim 1 wherein said at least one catheter means is selected from the group consisting of a catheter for the delivery of a drug, therapeutic agent, or biologic agent.

5. The method of claim 1 wherein said at least one catheter means is selected from the group consisting of a fluoroscopic catheter, an angiographic catheter, an endoscopic imaging catheter, an ultrasonic imaging catheter, and a mapping-guiding catheter.

6. The method of claim 1 wherein said at least one catheter means is a rotational angioplasty apparatus.

7. The method of claim 1 wherein said opening is a mini-thoracotomy or mini-stemotomy.

8. The method of claim 1 further comprising forming at least one entry site in a wall of a coronary lumen for the delivery of said catheter means to said target site.

9. The method of claim 8 wherein said coronary lumen is selected from the group consisting of an aorta, a subdlavian artery, a carotid artery, and an innominate artery.

10. The method of claim 8 wherein said at least one entry site is formed by puncturing a wall of said coronary lumen with an arterial access device comprising a cannula and an integral sealing member for atraumatically sealing said cannula within said at least one entry site upon puncturing.

11. The method of claim 10 wherein said step of delivering said at least one catheter means comprises the steps of inserting a distal end of said catheter means into said cannula and advancing said distal end through said coronary lumen to said target site.

12. The method of claim 1 wherein said at least one catheter means has a length not substantially more than 40 cm.

13. A method of treating coronary artery disease without cardiopulmonary bypass by performing a coronary artery bypass graft procedure on a beating heart through a minimally invasive incision of not substantially more than 12 cm in length in the thoracic cavity, the improvement comprising the additional contemporaneous steps comprising:

introducing at least one catheter means through the minimally invasive incision, establishing at least one catheter means entry site in a coronary lumen accessible through the minimally invasive incision, advancing said at least one of the catheter means to a target site in a coronary artery of a beating heart, treating or evaluating the condition of a target site in a coronary artery.

14. The method of claim 13 further comprising the step of withdrawing said at least one catheter means from the at least one catheter means entry site while the heart continues to beat.

15. The method of claim 13 wherein a minimally invasive coronary artery bypass graft procedure is performed on the same target site treated or evaluated with said at least one catheter means.

16. The method of claim 13 wherein a first target site is treated with said at least one catheter means and wherein a minimally invasive coronary artery bypass graft procedure is performed on a second target site.

17. A method of revascularizing more than one coronary artery on a beating heart without employing cardiopulmonary bypass, comprising the contemporaneous steps of:

forming a minimally invasive incision of not substantially more than 12 cm in length in a patient's thoracic cavity, performing a coronary artery bypass graft procedure on a first coronary artery accessible through the minimally invasive incision, establishing at least one catheter means entry site in a coronary lumen of a beating heart accessible through the minimally invasive incision, introducing at least one catheter means through the minimally invasive incision and advancing said catheter means through said at least one catheter means entry site to a target site in a second coronary artery of a beating heart, and revascularizing said target site in said second coronary artery of a beating heart.

* * * * *